United States Patent
Kelley et al.

(10) Patent No.: US 7,413,558 B2
(45) Date of Patent: Aug. 19, 2008

(54) ELASTICALLY DISTENSIBLE FOLDING MEMBER

(75) Inventors: Gregory S. Kelley, San Diego, CA (US); Dennis M. Vigil, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 665 days.

(21) Appl. No.: 10/848,270

(22) Filed: May 18, 2004

(65) Prior Publication Data

US 2005/0137617 A1   Jun. 23, 2005

Related U.S. Application Data

(63) Continuation-in-part of application No. 10/742,166, filed on Dec. 19, 2003, now Pat. No. 7,338,463.

(51) Int. Cl.
*A61M 29/00* (2006.01)

(52) U.S. Cl. .............. 604/103.08; 604/96.01; 604/103.07; 606/159; 606/170; 606/192

(58) Field of Classification Search ............ 604/96.01, 604/103.07, 103.08; 606/159, 170, 192
See application file for complete search history.

(56) References Cited

U.S. PATENT DOCUMENTS

| | | | |
|---|---|---|---|
| 4,685,458 A | 8/1987 | Leckrone |
| 4,710,181 A | 12/1987 | Fuqua |
| 4,966,604 A | 10/1990 | Reiss |
| 5,042,985 A | 8/1991 | Elliott et al. |
| 5,053,044 A | 10/1991 | Mueller et al. |
| 5,074,841 A | 12/1991 | Ademovic et al. |
| 5,078,725 A | 1/1992 | Enderle et al. |
| 5,092,872 A | 3/1992 | Segalowitz |
| 5,092,873 A | 3/1992 | Simpson et al. |
| 5,112,900 A | 5/1992 | Buddenhagen et al. |
| 5,116,318 A | 5/1992 | Hillstead |
| 5,156,610 A | 10/1992 | Reger |
| 5,176,693 A | 1/1993 | Pannek, Jr. |
| 5,209,799 A | 5/1993 | Vigil |
| 5,222,966 A | 6/1993 | Perkins et al. |
| 5,224,949 A | 7/1993 | Gomringer et al. |
| 5,320,634 A | 6/1994 | Vigil et al. |
| 5,336,234 A | 8/1994 | Vigil et al. |
| 5,348,538 A | 9/1994 | Wang et al. |
| 5,372,601 A | 12/1994 | Lary |
| 5,403,334 A | 4/1995 | Evans et al. |
| 5,403,340 A | 4/1995 | Wang et al. |
| 5,447,497 A | 9/1995 | Sogard et al. |
| 5,549,552 A | 8/1996 | Peters et al. |
| 5,550,180 A | 8/1996 | Elsik et al. |
| 5,556,383 A | 9/1996 | Wang et al. |

(Continued)

*Primary Examiner*—Nicholas D. Lucchesi
*Assistant Examiner*—Laura A Bouchelle
(74) *Attorney, Agent, or Firm*—Vidas, Arrett & Steinkraus, P.A.

(57) ABSTRACT

An elastically distensible folding member is disclosed. The folding member can be formed with a wall that is substantially shaped as a tube when the folding member is in a relaxed (i.e. unstressed) state. The tubular shaped folding member defines a tube axis and can have an axially aligned slit that extends through the wall. The folding member can be used to cover an incising element that is attached to the balloon and positioned in the lumen of the tubular folding member. During balloon inflation, the folding member can be deformed to expose the tip of the incising element to allow for a tissue incision.

20 Claims, 3 Drawing Sheets

U.S. PATENT DOCUMENTS

| | | |
|---|---|---|
| 5,556,405 A | 9/1996 | Lary |
| 5,616,149 A * | 4/1997 | Barath .................. 606/159 |
| 5,697,944 A | 12/1997 | Lary |
| 5,713,913 A | 2/1998 | Lary et al. |
| 5,728,123 A | 3/1998 | Lemelson et al. |
| 5,792,158 A | 8/1998 | Lary |
| 5,797,935 A | 8/1998 | Barath |
| 5,830,182 A | 11/1998 | Wang et al. |
| 5,941,869 A | 8/1999 | Patterson et al. |
| 5,951,941 A | 9/1999 | Wang et al. |
| 6,013,055 A | 1/2000 | Bampos et al. |
| 6,090,135 A | 7/2000 | Plaia et al. |
| 6,102,904 A | 8/2000 | Vigil et al. |
| 6,110,192 A | 8/2000 | Ravenscroft et al. |
| 6,146,356 A | 11/2000 | Wang et al. |
| 6,171,278 B1 | 1/2001 | Wang et al. |
| 6,258,108 B1 | 7/2001 | Lary |
| 6,306,151 B1 | 10/2001 | Lary |
| 6,309,399 B1 | 10/2001 | Barbut et al. |
| 6,328,925 B1 | 12/2001 | Wang et al. |
| 6,406,457 B1 | 6/2002 | Wang et al. |
| 6,488,693 B2 | 12/2002 | Gannoe et al. |
| 6,575,933 B1 | 6/2003 | Wittenberger et al. |
| 6,632,231 B2 | 10/2003 | Radisch, Jr. |
| 6,808,518 B2 * | 10/2004 | Wellman et al. ............ 604/507 |
| 2002/0151924 A1 * | 10/2002 | Shiber .................. 606/194 |
| 2005/0119678 A1 * | 6/2005 | O'Brien et al. ............. 606/159 |

* cited by examiner

ELASTICALLY DISTENSIBLE FOLDING MEMBER

This application is a continuation-in-part of application Ser. No. 10/742,166, filed Dec. 19, 2003, now U.S. Pat. No. 7,338,463 which is currently pending. The contents of application Ser. No. 10/742,166 are incorporated herein by reference.

FIELD OF THE INVENTION

The present invention pertains generally to medical devices. Some embodiments of the present invention pertain to catheters for the revascularization of coronary and peripheral vessels. The present invention is particularly, but not exclusively, useful as an incising balloon having sharp incising elements, such as atherotome blades or injectors, that are shielded when the balloon is deflated.

BACKGROUND OF THE INVENTION

Arterial blockages caused by the build up of plaque in the arteries of a patient can have grave consequences. Specifically, the build up of plaque in arteries can reduce and eventually block the flow of blood through the affected vessel. When blood flow is reduced in the coronary arteries, the heart muscle can become deprived of oxygen, and the patient is often prone to suffer angina. In severe cases of coronary artery blockage, the patient can suffer a heart attack.

Fortunately, many modern surgical techniques, such as percutaneous transluminal coronary angioplasty (PTCA), have been developed to alleviate the stenoses that are formed when plaque builds up in a patient's arteries. These procedures use a balloon angioplasty device to relieve arterial stenoses by compression of the stenosis. In angioplasty surgery, the balloon of a balloon catheter is initially attached to a catheter tube in a deflated configuration. The balloon is then inserted into and advanced through the vasculature of the patient until the balloon is positioned across the stenosis requiring treatment. Once the balloon has been properly positioned, fluid is infused into the balloon. As the balloon expands, it dilates the lumen of the artery and compresses the plaque. The balloon is subsequently deflated and, once in its deflated configuration, it is either withdrawn from the artery or placed across another stenosis, to restore normal blood flow through the artery.

A particular problem associated with an angioplasty procedure exists during the deflation stage of the balloon, prior to its removal from the artery. In greater detail, it is desirable that the balloon be deflated as tightly as practicable to facilitate its removal from the arterial passageways. Specifically, it is desirable to have the balloon collapse evenly and compactly during balloon deflation. Once deflated, the balloon catheter must often travel through tortuous passageways and it is, therefore, desirable to have the balloon deflate uniformly into a predictable configuration. If the balloon fails to deflate in a uniform manner, an irregular bulge in the balloon may cause difficulties in withdrawing the balloon catheter from the artery.

Although conventional percutaneous transluminal coronary angioplasty (PTCA) procedures have been somewhat effective in treating coronary artery disease, cutting balloons can also be an effective treatment option for the revascularization of both coronary and peripheral vessels. The cutting balloon mechanism is unique in that the balloon pressure is distributed over one or more blades (i.e. microtomes). The blade(s) function as stress concentrators and cut initiators in PTCA atherectomy procedures. In some cases, PTCA atherectomy procedures may be effective in reducing vessel recoil and vessel injury and in lowering the rate of restenosis, as compared to conventional PTCA procedures.

The atherotome blades used in cutting balloons are extremely sharp (e.g. three to five times sharper than a conventional scalpel). It is desirable that the blades do not tear, cut or perforate the inflation balloon during assembly of the cutting balloon, handling or during clinical use. In addition to balloon perforation concerns, an inadvertent incising of tissue as the cutting balloon is being moved through the vasculature is also undesirable.

Along these lines, a device having a blade-like structure which is described as a "parting edge" which is shielded within the pleats of an expandable clover leaf shaped tube is disclosed by Shiber in U.S. Patent application publication No. 2002/0151924, filed Oct. 17, 2002 and entitled "Clover Leaf Shaped Tubular Medical Device". However, the clover leaf design disclosed by Shiber does not necessarily protect the relatively fragile balloon from the "parting edges." This is because the "parting edges" are located within the pleats of the balloon leaving portions of the balloon exposed to the "parting edges" when the device is twisted, turned and bent through the curved vasculature of a patient.

In addition to the conventional PTCA treatments and PTCA atherectomy procedures described above, it is sometimes desirable to inject a medicament into a vessel wall. For example, U.S. Pat. No. 6,102,904 which issued to Vigil et al. on Aug. 15, 2000 for an invention entitled "Device for Injecting Fluid into a Wall of a Blood Vessel," and which is assigned to the same assignee as the present invention, discloses such a device. As disclosed in Vigil '904, the device includes an inflatable balloon that is mounted on a catheter and a plurality of injectors that extend outwardly from the balloon. A fluid passageway is provided to place each injector in fluid communication with a fluid source. During use of the device, the balloon is first positioned in a vessel proximate the treatment area. Next, the balloon is inflated to embed the injectors into the vessel wall. Subsequently, fluid from the fluid source is introduced into the fluid passageway and through the dispensers into the treatment area. Like the atherotome blades described above, it is desirable that the injectors do not tear, cut or perforate the inflation balloon during assembly of the cutting balloon, handling or during clinical use.

In light of the above, the present invention is directed to unique devices and methods for refolding the balloon of a balloon catheter. In addition, the present invention is directed to balloon refolding devices and corresponding methods of use which are relatively simple to implement and comparatively cost effective.

SUMMARY OF THE INVENTION

The present invention is directed to an elastically distensible folding member for use on the balloon of a balloon catheter. In one application of the present invention, the folding member can be used to refold a dilatation balloon during a balloon deflation to facilitate movement of the balloon through a body vessel. In another application, the folding member is used as a sheath to cover an incising element that is attached to an inflatable balloon during movement of the balloon through a body vessel. For example, the folding member can be used to protect an incising element such as a cutting blade, injector or round wire when the balloon is deflated and thereafter expose the incising element during a balloon inflation to incise target tissue at a treatment site in a body vessel of a patient. In a particular embodiment, the folding member can be used to protect the tip of an injector when the balloon is deflated and thereafter expose the injector tip during a balloon inflation to allow a medicament to be dispensed into a target tissue.

For use with the present invention, the catheter typically includes an elongated, inflatable balloon that defines a balloon axis in the direction of elongation. When deflated, the balloon can be somewhat easily passed through bodily conduits, such as a patient's vasculature, allowing the balloon to be advanced to and withdrawn from a treatment site. Once the balloon has been positioned at the treatment site, the balloon can be inflated into a radially expanded configuration. This balloon expansion can be used to dilate a vessel lumen, drive an incising element into a target tissue, or both.

In accordance with the present invention, each folding member is made of an elastic material and is formed with a wall that is substantially shaped as an elongated tube when the folding member is in a relaxed (i.e. unstressed) state. The tubular shaped folding member defines a tube axis in the direction of elongation and is formed with an axially aligned slit that extends radially through the wall. For the folding member, the slit establishes a pair of axially aligned edges that are substantially juxtaposed when the folding member is in the relaxed state.

One or more folding member(s) can be bonded to the outer surface of the inflatable balloon and oriented to align each tube axis substantially parallel with the balloon axis. With this cooperation of structure, the folding member is tubular shaped while the balloon is deflated and is elastically deformed during a balloon inflation. Specifically, during a balloon inflation, the folding member deforms from its tubular shape with the edges separating from their initial juxtaposed configuration. When the balloon is fully inflated, at least a portion of the folding member substantially conforms with the outer surface of the balloon which is typically cylindrical shaped at full inflation. After the tissue has been dilated, the balloon can be deflated, a process in which the folding member returns to its relaxed, tubular shape.

In one aspect of the present invention, the folding member can be used to cover a rigid, incising element that is mounted on the outer surface of the balloon. Specifically, for the present invention, each incising element has an incising tip and extends from the outer surface of the balloon to the incising tip. For example, the incising element can be a cutting blade that extends to a cutting edge or an injector that extends to an injector tip. For these embodiments, the tubular folding member is bonded to the outer surface of the balloon with the tip of the incising element positioned in the lumen of the tubular folding member (when the folding member is tubular shaped and in the relaxed state). With this cooperation of structure, the folding member covers the tip of the incising element when the balloon is deflated (and the folding member is relaxed).

When the balloon is inflated, the balloon can become taut and elastically deform the folding member. As a consequence, the folding member deforms from its initial, relaxed shape during balloon inflation and the edges separate from their initial juxtaposed configuration. Eventually, with continued balloon inflation, the folding member deforms until the tip of the incising element becomes exposed. Once exposed, the tip of the incising element can be driven into the target tissue. In a particular embodiment, the folding member can be used to protect the tip of an injector when the balloon is deflated and thereafter expose the injector tip during a balloon inflation to allow a medicament to be dispensed into a target tissue.

After the tissue has been incised (and in some cases injected with medicament), the balloon can be deflated, a process in which the folding member returns to its relaxed shape. During a balloon deflation, the folding member folds the balloon and, once relaxed, the folding member covers the tip of the incising element to prevent the inadvertent cutting of tissue and balloon perforation during withdrawal of the catheter from the treatment site.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
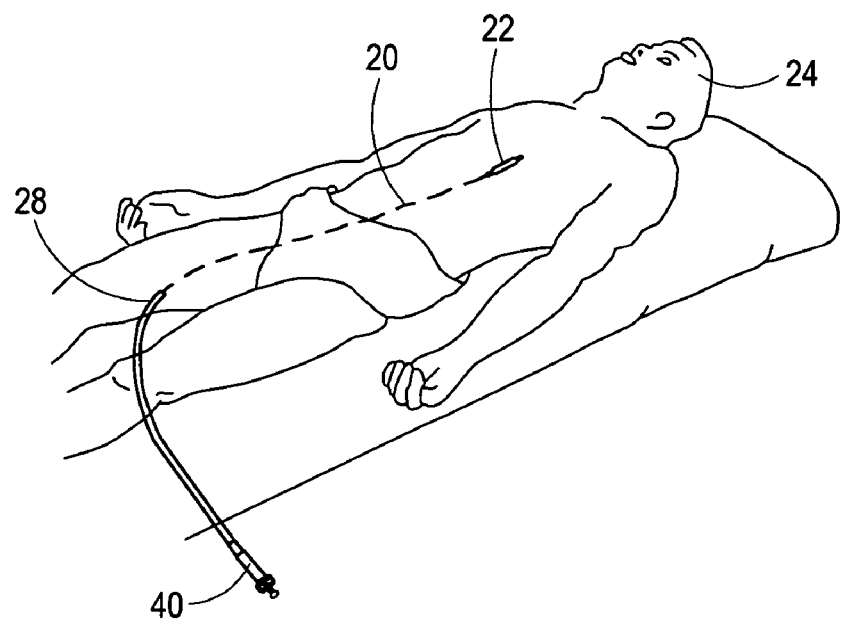
FIG. 1 is a simplified, perspective view of a catheter having an incising device operationally positioned in the upper body of a patient.

Referring initially to FIG. 1, a catheter 20 having an incising device 22 is shown for performing a medical procedure at an internal treatment site of a patient 24. More specifically, the catheter 20 is shown positioned to treat a lesion in an upper body artery of a human patient. Although the catheter 20 is capable of performing a medical procedure in an upper body artery such as a coronary artery, those skilled in the pertinent art will quickly recognize that the use of the catheter 20 as herein described is not limited to use in a specific artery, but, instead can be used in vascular conduits and other ductal systems (e.g. a bile duct or urinary tract) throughout the human body. Moreover, although FIG. 1 shows the catheter 20 used in a human body, it is to be appreciated that the catheter 20 can also be used in non-humans (e.g. animals) if desired. Functionally, the catheter 20 is configured to incise a biological material from within a body conduit. As used herein, the term "biological material" and its derivatives includes, but is not limited to, cellular matter including tissue (diseased, healthy or otherwise), deposits such as cholesterol and calcium deposits, and lesions which, for example, may consist of cellular matter and/or deposits.

Figure 2:
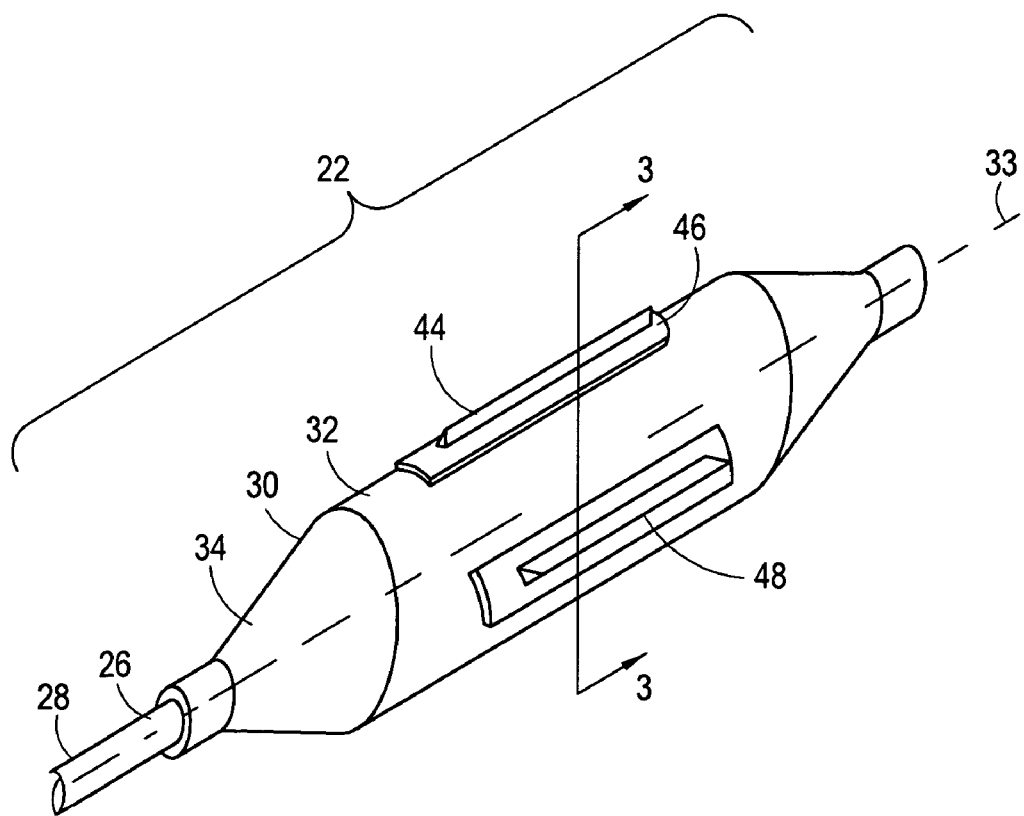
FIG. 2 is an enlarged, perspective view of an incising device, shown with the balloon inflated.

Referring now to FIG. 2, it can be seen that the incising device 22 is attached to the distal end 26 of a catheter tube 28. FIG. 2 further shows that the incising device 22 can include an inflatable balloon 30 that typically includes a cylindrical shaped working section 32 that defines an axis 33.

For the catheter 20, the inflatable balloon 30 can be made of a compliant, semi-compliant or non-compliant material. Specifically, any suitable thermoplastic or thermosetting material may be used in accordance herewith including both elastomeric and non-elastomeric materials. Thermoplastic materials find particular utility herein. Examples of non-elastomeric materials include, but are not limited to, polyolefins including polyethylene and polypropylene, polyesters, polyethers, polyamides, polyurethanes, polyimides, and so forth, as well as copolymers and terpolymers thereof. As used herein, the term "copolymer" shall hereinafter be used to refer to any polymer formed from two or more monomers.

Examples of suitable elastomeric materials include, but are not limited to, elastomeric block copolymers including the styrenic block copolymers such as styrene-ethylene/butylene-styrene (SEBS) block copolymers disclosed in U.S. Pat. No. 5,112,900 which is incorporated by reference herein in its entirety. Other suitable block copolymer elastomers include, but are not limited to, styrene-isoprene-styrene (SIS), styrene-butadiene-styrene (SBS), styrene-isobutylene-styrene (SIBS) and so forth. Block copolymer elastomers are also described in commonly assigned U.S. Pat. Nos. 6,406,457, 6,171,278, 6,146,356, 5,951,941, 5,830,182 and 5,556,383, each of which is incorporated by reference herein in its entirety.

Elastomeric polyesters and copolyesters may be employed herein. Examples of elastomeric copolyesters include, but are not limited to, poly(ester-block-ether) elastomers, poly(ester-block-ester) elastomers and so forth. Poly(ester-block-ether) elastomers are available under the trade name of HYTREL® from DuPont de Nemours & Co. and consist of hard segments of polybutylene terephthalate and soft segments based on long chain polyether glycols. These polymers are also available from DSM Engineering Plastics under the trade name of ARNITEL®.

Non-elastomeric polyesters and copolymers thereof may be employed, such as the polyalkylene naphthalates, including polyethylene terephthalate and polybutylene terephthalate, for example. Polyamides including nylon, and copolymers thereof, such as poly (ether-block-amides) available under the trade name of PEBAX® from Atofina Chemicals in Philadelphia, Pa., are suitable for use herein. Suitable balloon materials are described in commonly assigned U.S. Pat. Nos. 5,549,552, 5,447,497, 5,348,538, 5,550,180, 5,403,340 and 6,328,925, each of which is incorporated by reference herein in its entirety. The above lists are intended for illustrative purposes only, and shall not be construed as a limitation on the scope of the present invention.

Figure 3:
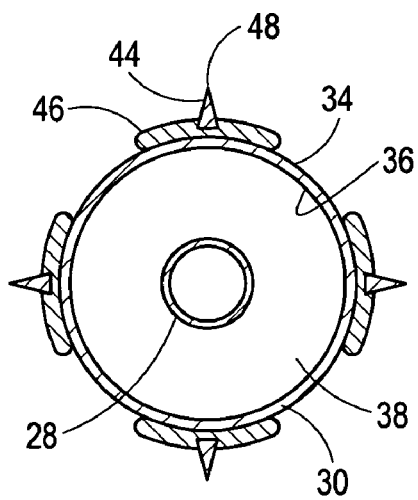
FIG. 3 is a cross-sectional view of the incising device shown in FIG. 2 as seen along line 3-3 in FIG. 2.

As best seen in FIG. 3, the inflatable balloon 30 can be characterized as having an outer surface 34 and an opposed inner surface 36 that surrounds an inflation volume 38 which can be infused with a medical grade fluid to expand the inflatable balloon 30. More specifically, as shown in FIG. 1, an inflation device, such as the syringe 40, can be used to pass a medical grade fluid through the catheter tube 28 to expand the inflatable balloon 30.

Cross-referencing FIGS. 2 and 3, it can be seen that the incising device 22 further includes a plurality of incising elements which in this case are elongated atherotome blades 44. For the catheter 20, the incising element is typically made of a material which is harder than the targeted biological material allowing the incising element to slice or break-apart the biological material. These materials can include, but are not limited to metals, ceramics, polymers such as hardened polymers, composite materials and combinations thereof. For example, the blade 44 can be made of a medical grade stainless steel.

For the embodiment shown, four longitudinally aligned blades 44 are uniformly distributed around the circumference of the working section 32 of the inflatable balloon 30. Typically, each blade 44 is made of a medical grade metal such as stainless steel. As best seen in FIG. 3, a portion of each blade 44 is embedded in a respective elastic folding member 46, thereby affixing the blade 44 to the respective folding member 46. From the folding member 46, each blade 44 extends radially to a sharp cutting edge 48. For the catheter 20, the blade 44 can be formed with a straight, uniform cutting edge 48, as shown, and can be formed with notches, serrations, or any other cutting edge feature known in the pertinent art.

Figure 4:
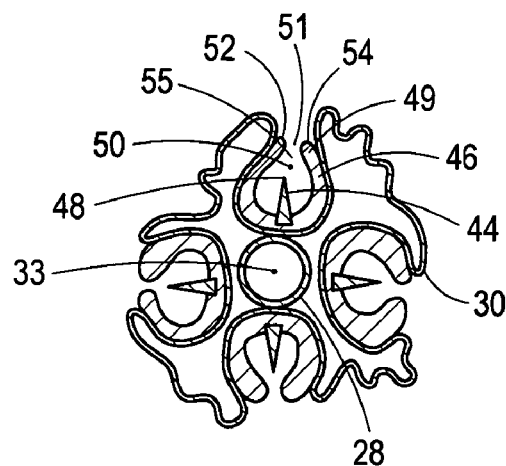
FIG. 4 is a cross-sectional view as would be seen along line 3-3 in FIG. 2 showing the incising device after the balloon has been deflated.

A better understanding of the folding member 46 can be obtained with cross-reference to FIGS. 2-4. For the incising device 22, the folding member 46 is made of a flexible, elastic material, such as one of the polymeric materials described above. Also, as best seen in FIG. 4, each folding member 46 is formed with a wall 49 that is substantially shaped as an elongated tube when the folding member 46 is in a relaxed (i.e. unstressed) state. The tubular shaped folding member 46 defines a tube axis 50 in the direction of elongation and is formed with an axially aligned slit 51 that extends radially through the wall 49. As further shown in FIG. 4, the slit 51 establishes a pair of axially aligned edges 52, 54 that are substantially juxtaposed when the folding member 46 is in the relaxed state. The tubular shaped folding member 46 also defines a tube lumen 55, as shown.

Continuing with FIG. 4, the folding member 46 is bonded to the outer surface 34 of the balloon 30 and oriented to align the tube axis 50 substantially parallel to the balloon axis 33. With this cooperation of structure, the folding member 46 covers and protects the cutting edge 48 of the blade 44 when the balloon 30 is deflated (and the folding member 46 is relaxed), as shown in FIG. 4. More specifically, as shown in FIG. 4, the folding member 46 extends radially beyond the cutting edge 48 of the blade 44 (which is positioned in the lumen 55) to cover and protect the cutting edge 48. For the embodiment shown in FIGS. 3 and 4, the blade 44 is embedded in the folding member 46 at a location that is substantially midway between the edges 52, 54.

As best seen in FIG. 3, when the balloon 30 is inflated, the balloon 30 elastically deforms the folding member 46 to substantially conform to the shape of the outer surface 34 of the inflated balloon 30. Comparing FIG. 3 with FIG. 4, it can be seen that the folding member 46 deforms from its initial tubular, relaxed shape when the balloon 30 is in a deflated state (FIG. 4) to a shape wherein the edges 52, 54 have separated from their initial juxtaposed configuration when the balloon 30 is in an inflated state (FIG. 3). It is to be appreciated that at some point during a balloon inflation, the folding member 46 distends sufficiently to expose the cutting edge 48 to thereby allow the sharp cutting edge 48 to be driven into the target tissue. This can be accomplished, for example, by further inflation of the balloon 30.

After the tissue has been incised by the cutting edge 48, the balloon 30 can be deflated. With the balloon 30 deflated, the folding member 46 returns to its relaxed shape as shown in FIG. 4. During deflation of the balloon 30, the folding member 46 folds the balloon 30 onto the catheter tube 28 (as shown in FIG. 4) to facilitate removal of the incising device 22 from the patient 24 (see FIG. 1). Because the folding member 46 covers and protects the cutting edge 48, inadvertent cutting of tissue is prevented and balloon perforation is avoided during retrieval of the incising device 22 from the treatment site.

Figure 5:
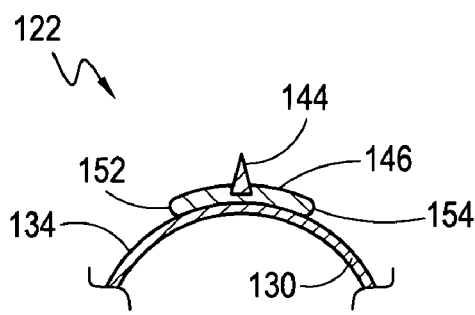
FIG. 5 is a cross-sectional view as would be seen along line 3-3 in FIG. 2 showing a portion of an alternate embodiment of an incising device in which the incising element is positioned closer to one axially aligned edge of the folding member than the other axially aligned edge of the folding member, shown with the balloon in the inflated state.
Figure 6:
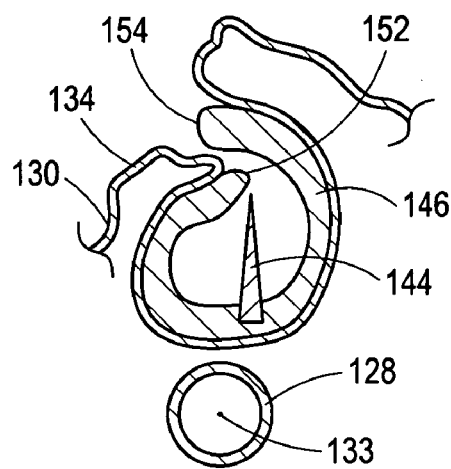
FIG. 6 is a cross-sectional view as would be seen along line 3-3 in FIG. 2 of the embodiment shown in FIG. 5, shown with the balloon in the deflated state.

FIG. 5 illustrates an alternate embodiment of an incising device 122 in which a portion of the incising element (i.e. atherotome blade 144) is embedded in the protective folding member 146 at a position that is closer to edge 152 of the folding member 146 than edge 154 of the folding member 146. As shown, the folding member 146 is bonded to the outer surface 134 of the inflatable balloon 130. FIG. 6 shows the folding member 146 in the relaxed state, with the balloon 130 deflated and folded on the catheter tube 128. As shown there, with the folding member 146 in the relaxed state, the edge 154 is juxtaposed with edge 152 and the edge 154 is positioned at a larger radial distance from the axis 133 than the edge 152. In some cases, the edge 154 can overlap with the edge 152, as shown.

Figure 7:
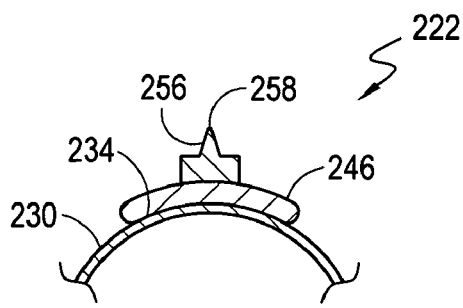
FIG. 7 is a cross-sectional view as would be seen along line 3-3 in FIG. 2 showing an embodiment of an incising device in which the incising element is an injector for injecting a medicament into selected tissue at a treatment site, shown with the balloon in the inflated state.
Figure 8:
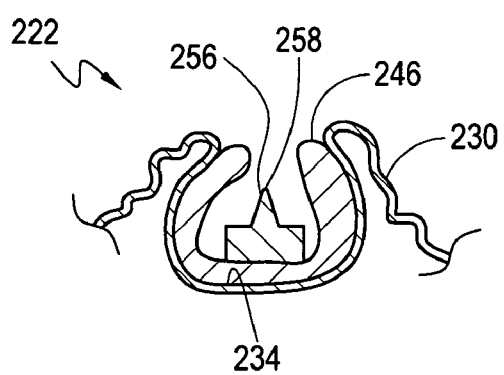
FIG. 8 is a cross-sectional view as would be seen along line 3-3 in FIG. 2 of the embodiment shown in FIG. 7, shown with the balloon in the deflated state.

FIG. 7 illustrates another embodiment of an incising device 222 in which the incising element is an injector 256 for injecting a medicament into selected tissue at a treatment site. The injector 256 is typically part of an injector strip which is aligned longitudinally on the balloon 230 and includes a plurality of injectors 256. The injector strip is placed in fluid communication with a fluid pump (not shown) and fluid medicament source (not shown), which can then be used to pump a medicament through each injector 256 and into selected tissue. As shown, the injector 256 is mounted on a folding member 246 and extends therefrom to an injector tip 258, which is typically sharp to allow the tip 258 to incise tissue and embed a portion of the injector 256 in the selected tissue. As shown, the folding member 246 is bonded to the outer surface 234 of the balloon 230. FIG. 8 shows the tubular folding member 246 in the relaxed state, with the balloon 230 deflated and folded. As shown there, with the folding member 246 in the relaxed state, the tubular folding member 246 covers the sharp injector tip 258 to prevent inadvertent cutting of tissue and balloon perforation during retrieval of the incising device 222 from the treatment site.

In alternate embodiments of the catheter 20, the incising element can have a shape other than a blade shape or injector. In particular, any incising element that extends to an operative surface feature capable of slicing or breaking apart biological material can be used. For example, the incising element can be formed as a round wire (not shown).

Figure 9:
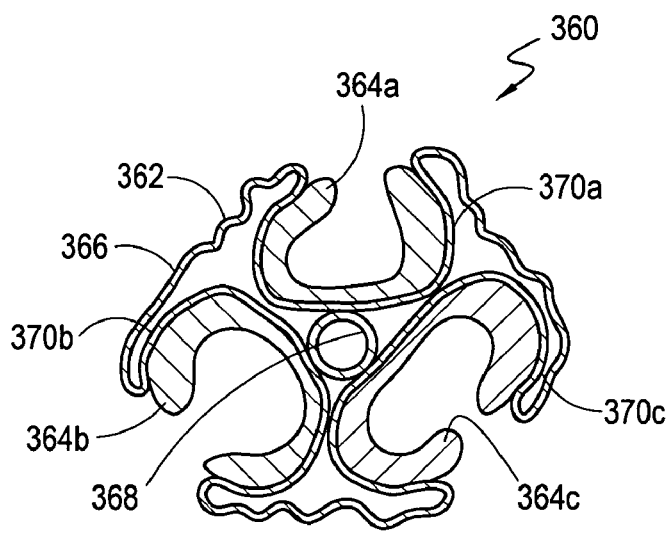
FIG. 9 is a cross-sectional view as would be seen along line 3-3 in FIG. 2 showing another embodiment of a refolding device for an angioplasty balloon, shown with the balloon in the deflated state.
Figure 10:
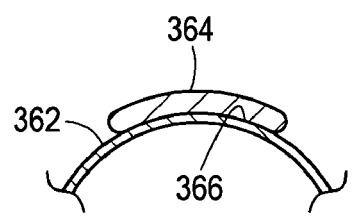
FIG. 10 is a cross-sectional view as would be seen along line 3-3 in FIG. 2 of the embodiment shown in FIG. 9, shown with the balloon in the inflated state.

FIGS. 9 and 10 illustrate a refolding device 360 for an angioplasty balloon 362. As shown, the refolding device 360 includes folding members 364a-c which are bonded to the outer surface 366 of the angioplasty balloon 362. For the refolding device 360, each folding member 364a-c is made of an elastic material. FIG. 9 shows the folding members 364a-c in the relaxed, tubular state, with the balloon 362 deflated and folded onto catheter tube 368. As shown there, when the folding members 364a-c are in the relaxed state, a respective first surface portion 370a-c of each folding member 364a-c is convex and folds the angioplasty balloon 362 into a respective pleat. Together, the folding members 364a-c fold the angioplasty balloon 362 onto the catheter tube 368 (as shown in FIG. 9) to facilitate removal of the angioplasty balloon 362 from the patient. On the other hand, as shown in FIG. 10, when the angioplasty balloon 362 is inflated, the folding member 364 elastically deforms to conform to the outer surface 366 of the inflated angioplasty balloon 362.

While the particular Elastically Distensible Folding Member and corresponding methods of use as herein shown and disclosed in detail are fully capable of providing the advantages herein before stated, it is to be understood that they are merely illustrative of the presently preferred embodiments of the invention and that no limitations are intended to the details of construction or design herein shown other than as described in the appended claims.

What is claimed is:

1. An incising device for use on a medical catheter to incise biological material at a treatment site, said incising device comprising:

a balloon defining a balloon axis, said balloon being inflatable from a first deflated configuration to a second radially expanded configuration;

an elongated incising element having an incising tip and mounted on said balloon to extend radially therefrom when said balloon is in said radially expanded configuration; and an elastic folding member having a substantially tubular shape when said folding member is in a relaxed state, said folding member being bonded to said outer surface of said balloon and sized to cover said tip when said balloon is deflated, said folding member being oriented on said balloon and formed with an axially aligned slit, with said folding member deforming in response to a balloon inflation to expose said incising tip for incision of the biological material;

wherein said folding member extends from a first axially aligned edge to a second axially aligned edge and said incising element is positioned closer to said first edge than said second edge to overlap said first and second edges when said balloon is in said deflated configuration.

2. An incising device as recited in claim 1 wherein said incising element is a cutting blade and said incising tip is a cutting edge.

3. An incising device as recited in claim 2 wherein said cutting blade is elongated and oriented on said balloon longitudinally.

4. An incising device as recited in claim 2 wherein a portion of said cutting blade is embedded in said folding member.

5. An incising device as recited in claim 1 wherein said incising element is an injector.

6. An incising device as recited in claim 1, further comprising a plurality of incising elements and a plurality of said folding members.

7. An incising device as recited in claim 6, wherein said folding members are uniformly distributed around the circumference of the balloon.

8. An incising device for use on a medical catheter to incise biological material at a treatment site, said device comprising:

an elongated balloon having an outer surface and defining a longitudinal balloon axis, said balloon being inflatable from a first deflated configuration to a second radially expanded configuration;

an incising element having an incising tip and mounted on said outer surface of said balloon; and an elastic folding member mounted on said outer surface of said balloon and having a wall that is substantially tubular shaped when said balloon is in said deflated configuration, said folding member formed with an axially aligned slit that extends through said wall to establish first and second axially aligned edges with said first edge being substantially juxtaposed with said second edge when said balloon is in the deflated configuration, said incising element positioned closer to said first edge than said second edge to overlap said first and second edges when said balloon is in said deflated configuration, wherein said folding member is oriented on said balloon with a tube axis substantially parallel to said balloon axis in said deflated configuration, and wherein said wall is non-tubular when said balloon is in said radially expanded configuration.

9. An incising device as recited in claim 8 wherein said incising element is a cutting blade and said incising tip is a cutting edge.

10. An incising device as recited in claim 9 wherein said cutting blade is elongated and oriented on said balloon longitudinally.

11. An incising device as recited in claim 9 wherein a portion of said cutting blade is embedded in said folding member.

12. An incising device as recited in claim 8 wherein said incising element comprises an injector.

13. An incising device as recited in claim 8, further comprising a plurality of incising elements and a plurality of said folding members.

14. An incising device as recited in claim 13, wherein said folding members are uniformly distributed around the circumference of the balloon.

15. A catheter comprising:
a catheter tube;
an elongated inflatable balloon mounted on said catheter tube, said balloon having an outer surface and defining a balloon axis in the direction of balloon elongation; and
an elastic folding member having a wall that is substantially tubular shaped in a relaxed state, said tube defining a tube axis and having a first edge and a second edge; said folding member being bonded on said outer surface of said balloon with said tube axis substantially parallel to said balloon axis, wherein said wall is substantially convex with respect to said balloon axis and said first edge overlaps said second edge when said balloon is deflated, and said wall is substantially concave with respect to said balloon axis when said balloon is inflated.

16. A catheter as recited in claim 15 wherein said tube shaped wall establishes a tube lumen and said catheter further comprises an incising element having an incising tip and mounted on said balloon and extending therefrom with said incising tip positioned in said tube lumen when said folding member is in the relaxed state to protect said incising tip during transit to a treatment site, the incising element positioned closer to said first edge than said second edge.

17. A catheter as recited in claim 16 wherein said incising element is a cutting blade and said incising tip is a cutting edge.

18. A catheter as recited in claim 17 wherein said catheter tube defines a longitudinal axis, said cutting blade is elongated, and said cutting blade is oriented on said balloon substantially parallel to said longitudinal axis.

19. A catheter as recited in claim 17 wherein at least a portion of said cutting blade is embedded in said folding member.

20. A catheter as recited in claim 16 wherein said incising element is an injector.

* * * * *